United States Patent [19]

Shalaby et al.

[11] 4,105,034

[45] Aug. 8, 1978

[54] POLY(ALKYLENE OXALATE) ABSORBABLE COATING FOR SUTURES

[75] Inventors: Shalaby W. Shalaby, Long Valley; Dennis D. Jamiolkowski, Paterson, both of N.J.

[73] Assignee: Ethicon, Inc., Somerville, N.J.

[21] Appl. No.: 805,501

[22] Filed: Jun. 10, 1977

[51] Int. Cl.$^2$ ............................................. A61L 17/00
[52] U.S. Cl. ................................... 128/335.5; 424/19; 427/2; 428/375; 428/378
[58] Field of Search ........................ 128/335.5; 424/19; 427/2; 428/375, 378

[56] References Cited

U.S. PATENT DOCUMENTS

| | | | |
|---|---|---|---|
| 3,322,125 | 5/1967 | Kurtz | 427/2 |
| 3,527,650 | 9/1970 | Block | 427/2 |
| 4,027,676 | 6/1977 | Mattei | 428/378 |
| 4,043,344 | 8/1977 | Landi et al. | 128/335.5 |

FOREIGN PATENT DOCUMENTS 2,139,455  2/1972  Fed. Rep. of Germany ............. 427/2

*Primary Examiner*—Benjamin R. Padgett
*Assistant Examiner*—Christine M. Nucker
*Attorney, Agent, or Firm*—Wayne R. Eberhardt

[57] ABSTRACT

The tie-down properties of multifilament surgical sutures are improved by coating the suture with an absorbable composition comprising a poly(alkylene oxalate) wherein the alkylene is a $C_6$ or a mixture of $C_4$ to $C_{12}$ alkylene moieties. Braided sutures coated with from about 1 to 15 percent by weight of the composition are characterized by a smooth knot tie-down under both wet and dry conditions.

33 Claims, No Drawings

4,105,034

POLY(ALKYLENE OXALATE) ABSORBABLE COATING FOR SUTURES

BACKGROUND OF THE INVENTION

1. Field of the Invention

This invention relates to an absorbable composition useful as a coating and lubricating finish for surgical sutures. More particularly, this invention relates to a means for improving the tie-down properties of synthetic absorbable multifilament sutures by coating the sutures with an absorbable lubricating composition.

2. Description of Prior Art

Suture materials are generally classified as either absorbable or nonabsorbable, with each type of suture material being preferred for certain applications. Absorbable suture materials are preferred for internal wound repair in which the sewn tissues will hold together after healing without suture reinforcement and in which a nonabsorbed suture may promote tissue irritation or other adverse bodily reaction over an extended period of time. Suture materials are considered to be absorbable if they disappear from the sewn tissue within about a year after surgery, but many absorbable suture materials disappear within shorter periods.

The earliest available absorbable suture materials were catgut and extruded collagenous materials. More recently, absorbable sutures derived from synthetic polymers have been developed which are strong, dimensionally uniform, and storage-stable in the dry state. Typical of such polymers are lactide homopolymers and copolymers of lactide and glycolide such as those disclosed in U.S. Pat. No. 3,636,956, and glycolide homopolymers such as those disclosed in U.S. Pat. Nos. 3,297,033 and 3,565,869, all these patents being incorporated herein by reference.

Monofilament synthetic absorbable suture materials are generally stiffer than their catgut or collagen counterparts, and synthetic absorbable sutures are therefore usually employed in a multifilament, braided construction in order to provide the suture with the desired degree of softness and flexibility. Such multifilament sutures exhibit a certain degree of undesirable roughness of "grabbiness" in what has been termed their "tie-down" performance, i.e., the ease or difficulty of sliding a knot down the suture into place.

Multifilament, nonabsorbable sutures such as braided sutures of polyethylene terephthalate, for example, can be improved with respect to tie-down performance by coating the external surface of the suture with solid particles of polytetrafluoroethylene and a binder resin as disclosed in U.S. Pat. No. 3,527,650. This procedure, however, is undesirable as applied to absorbable sutures because polytetrafluoroethylene is nonabsorbable and sutures coated therewith would leave a polymer residue in the sewn tissue after the suture had absorbed.

Multifilament, nonabsorbable sutures can also be improved with respect to tie-down performance by coating them with a linear polyester having a molecular weight between about 1,000 and about 15,000 and at least two carbon atoms between the ester linkages in the polymer chain as disclosed in U.S. Pat. No. 3,942,532. This patent discloses that the aforementioned polyesters may also be used to coat absorbable synthetic sutures but does not consider that such coated sutures would not be totally absorbable.

The aforementioned U.S. Pat. No. 3,297,033, discloses that the synthetic absorbable sutures described therein may be coated with conventional suture coating materials such as a silicone or beeswax in order to modify the handling or absorption rate of the sutures. These coating materials are not readily absorbable, however, and will accordingly leave an undesirable residue in the tissue after the suture itself is absorbed.

It is accordingly an object of the present invention to provide an absorbable, lubricating coating for multifilament sutures of braided, twisted, or covered construction. It is a further object of this invention to provide an absorbable coating to improve the tie-down properties of such multifilament sutures. It is a yet further object of this invention to provide a wholly absorbable coated synthetic multifilament suture having good tie-down properties.

SUMMARY OF THE INVENTION

In accordance with the present invention, there is provided as a coating for sutures, particularly synthetic absorbable multifilament sutures, an absorbable polymeric composition comprising poly(alkylene oxalates) wherein the alkylene moieties are derived from $C_6$ or mixtures of $C_4$ to $C_{12}$ diols. The polymers are preferably applied to the suture from a solvent solution to provide a final coating add-on of from about 1 to 15 percent by weight of the suture.

The alkylene oxalate polymers are conveniently prepared from diethyl oxalate and hexanediol or a mixture of $C_4$ to $C_{12}$ alkanediols. Preferred polymers are those which have a melting point below about 100° C, an inherent viscosity (as hereafter defined) of from about 0.1 to 1.2 and a crystallinity of at least about 15 percent. The coating is particularly useful for improving the handling and tie-down smoothness of braided sutures prepared from homopolymers and copolymers of lactide and glycolide, and other absorbable polymers.

DESCRIPTION OF PREFERRED EMBODIMENT

The poly(alkylene oxalate) compositions of the instant invention may be applied to any suture material where it is desired to improve fiber lubricity, suture tie-down characteristics, or the like. The coating is particularly useful with synthetic absorbable multifilament sutures such as polylactide, polyglycolide, copolymers of lactide and glycolide, poly(p-dioxanone), and mixtures of such polymers with each other and with other compatible absorbable compositions as those described, for example, in U.S. Pat. Nos. 3,636,952 and 2,683,136, which patents are herewith incorporated herein by reference. Suture compositions based upon lactide and glycolide are sometimes referred to herein simply as homopolymers and copolymers of lactide and glycolide.

In a preferred embodiment of the present invention, the poly(alkylene oxalate) coating is applied to the suture surface as a solution of the polymer in a volatile solvent such as chloroform or a mixture of chloroform and trichloroethane, followed by drying to remove the solvent. The coating may be applied to the suture by any suitable process such as passing the suture through a solution of the polymer composition or over a brush or applicator wetted with the solution, or past one or more spray nozzles dispensing the solution as droplets. The suture wetted with the coating solution is subsequently dried for a time and at a temperature sufficient to volatilize the solvent and leave a residue of polymer on the surface of the suture.

In place of a coating solution, the poly(alkylene oxalate) polymer may be applied to the surface of the suture by passing the suture over or between solid blocks of the polymer which is then transferred to the surface of the suture by a rubbing action, possibly accompanied by localized melting. In addition, molten or plasticized coating material may be applied directly onto the surface of the suture by known techniques.

In coating multifilament sutures with the compositions of this invention, it is not necessary that every filament within the suture be individually or completely coated. In most instances, however, the coating composition will penetrate into the suture structure, particularly when the coating composition is applied as a solvent solution.

The coating composition may, if desired, also contain components other than those discussed above for other useful purposes including dyes, antibiotics, antiseptics, anesthetics and anti-inflammatory agents.

The amount of coating composition applied to the fiber, i.e., the coating add-on, may be increased or decreased by controlling the method of application, e.g., the concentration of polymer in the coating solution, the rate of application to the suture, and the like. In general, the coating composition applied to a braided suture will preferably constitute from about 2 to about 10 percent by weight of the coated fiber, but coating add-on may range from as little as about 1 percent by weight to as much as about 15 percent or higher in some cases. As a practical matter, and for reasons of economy and general performance, it is generally preferred to apply the minimum amount of coating consistent with good tie-down performance, and this level of add-on is readily determined experimentally for any particular fiber-coating system.

The improvement in tie-down properties imparted to synthetic absorbable sutures may be determined semi-quantitatively by comparing the feel of coated and uncoated sutures during the act of tying down a single throw knot. Suture tie-down roughness is graded from 0 to 10 with 0 being comparable to an uncoated suture and 10 indicating no detectable roughness. Roughness values above 4 are considered acceptable, while values of 7 or higher are comparable to conventional silicon-coated silk and are considered fully satisfactory.

Suture tie-down roughness may also be quantitatively determined by an instrumental test method using an Instron Tester coupled with a high speed Sanborn Occillographic Recorder as described in U.S. Pat. No. 3,942,532, incorporated herein by reference.

Suture tie-down properties are preferably determined on both wet and dry sutures since many suture materials have different tie-down characteristics when tested wet or dry. Tie-down properties are preferably evaluated dry after the sutures have been conditioned for at least 2 days in a vacuum drying oven at room temperature and 100 microns absolute pressure, and wet after being immersed in water at 25° C for 1 minute.

The alkylene oxalate polymers of the present invention are conveniently and preferably prepared by reacting diethyl oxalate with hexanediol or a mixture of $C_4$ to $C_{12}$ alkanediols to obtain polymers which melt below 100° C and have an inherent viscosity between about 0.1 and 1.2 as determined at 25° C on a 0.1 percent solution (1 g/l) of polymer in cloroform ($CHCl_3$) or hexafluoroisopropanol (HFIP). Particularly preferred polymers are those melting within the range of 40° to 70° C and having an inherent viscosity of 0.1 to 0.5.

The low melting temperatures of the poly(alkylene oxalate) polymers useful in the present invention may allow the polymer coating on the suture to melt by friction-induced heating to form a low to moderate viscosity liquid interface between the suture strands as the suture is tied down according to standard surgical practice. Such a liquid interface provides minimum friction at the actual contact area between the sliding sutures. The linear symmetrical polymer chains are highly crystallizable, allowing the liquid interface to resolidify immediately as the sutures separate and the surface cools. The coated sutures thereby maintain the integrity of the coating upon repeated sliding and there is little tendency for the coating material to crack or flake off the suture.

The preferred poly(alkylene oxalate) polymers of the present invention are those wherein the alkylene moieties are derived from $C_6$ or a mixture of $C_4$ to $C_{12}$ alkanediols. In the case of two component mixtures, e.g., mixtures of $C_4$ and $C_6$, $C_4$ and $C_8$, $C_4$ and $C_{10}$, $C_6$ and $C_8$, $C_6$ and $C_{10}$, $C_6$ and $C_{12}$, and the like, each component is present in an amount equal to from about 10 to 90 percent of the total polymer. In the case of a preferred three-component mixture of $C_4$-, $C_6$-, and $C_8$-alkylene oxalates, the $C_6$ component comprises from about 30 to 80 percent of the total poly(alkylene oxalate), and the $C_4$ and $C_8$ components each comprise from about 10 to 40 percent of the total polymer. One preferred multi-component poly(alkylene oxalate) is composed of a mixture of $C_4$-, $C_6$-, $C_8$- and $C_{12}$-alkylene oxalate moieties wherein each component comprises from about 10 to 40 percent of the total.

The following examples are provided to further illustrate the method and product of the present invention. Unless otherwise stated, all parts and percentages are by weight. In these examples, inherent viscosity ($\eta$inh) was determined on a 0.1 percent solution of polymer in chloroform or hexafluoroisopropanol (HFIP) at 25° C as above described. A DuPont 990 DSC apparatus was used to determine the melting temperature ($T_m$) of the polymers in nitrogen using 10 mg samples and a heating rate of 10° or 20° C/min, as specified in the example. Crystallinity was determined by the method of Hermans and Weidinger and the diffractometer patterns were resolved with a DuPont 310 curve analyzer.

Braided sutures were coated with the poly(alkylene oxalate) polymers of the present invention by passing the suture over a series of rollers submerged in a solution of the polymer in a suitable solvent. The solvent was removed by evaporation and the coated suture wound on a spool for evaluation.

The coated sutures were evaluated for tie-down smoothness semiquantitatively and/or instrumentally as hereinbefore described. The coatings on the suture were subjectively evaluated for appearance, lack of skinning during tie-down, and lack of cracking during handling.

To evaluate the tissue response of coated sutures, two 2-centimeter segments of sterile suture were implanted into both left and right gluteal muscles of female Long-Evans rats. The implant sites were recovered after 3, 7 and 28 days, and muscle cross sections were examined microscopically for tissue reaction.

To determine the effect of the coating on the rate of absorption of the suture, two segments of suture were implanted in the abdominal subcutis of young (100 g) female rats. The segments were placed parallel to and about 1.5 cm to each side of the midline. The rats were examined weekly or biweekly for 14 weeks. The amount of suture remaining was calculated for each sample at each inspection period, and the time in weeks when 50 and 10 percent of the suture remained was determined graphically.

EXAMPLE 1

Poly(hexamethylene oxalate)

Distilled dibutyl oxalate (20.2 g, 0.100 mole), 1,6-hexanediol (16.2 g, 0.137 mole) and tetraisopropylorthotitanate (0.01M in toluene, 0.3 ml, 0.003 mmole) were added under dry and oxygen-free conditions to a glass reactor equipped for stirring. The mixture was heated under nitrogen at 140°, 160°, and 170° C for 1, 1, and 17 hours, respectively, while allowing the formed butanol to distill. The prepolymer was allowed to cool, then reheated in vacuo (0.05 mm Hg) to 160° C. The reactor was maintained at 160°, 170°, 180°, and 200° C for 0.5, 1.5, 1, and 3 hours, respectively, while continuously removing distillates. The polymer was cooled, isolated, and stored in vacuo. Properties of the resulting polymer are given in Table I.

The polymer was dissolved in chloroform to a concentration of 20 g polymer per 100 ml solvent. A size 2-0 braided absorbable surgical suture composed of a copolymer derived from 90 percent glycolide and 10 percent lactide was coated with the polymer solution as hereinbefore described to obtain a final polymer coating add-on of 13 percent based on the weight of the dried suture. Additional samples of coated sutures having different levels of coating add-on were prepared by varying the solvent, the polymer concentration in the coating solution, and the coating application rate. Descriptions of the prepared sutures and results of the suture evaluation are given in Table II.

EXAMPLE 2

79/21 Poly(decamethylene-co-tetramethylene oxalate)

Following the procedure of Example 1, distilled dibutyl oxalate (26.3 g, 0.130 mole), distilled 1,10-decanediol (34.8g, 0.200 mole), 1,4-butanediol (4.9 g, 0.054 mole) and tetraisopropylorthotitanate (0.01M in toluene, 0.5 ml, 0.005 mmole) were added under dry and oxygen-free conditions to a glass reactor equipped for stirring. The mixture was heated under nitrogen at 150° and 165° C for 1.5 and 1 hour, respectively, while allowing the formed butanol to distill. The pressure was reduced (0.1 mm) and the prepolymer heated and maintained at 175°, 180° and 200° C for 16, 2 and 5 hours, respectively, while continuing to collect distillates. The resulting polymer, having the properties described in Table I, was dissolved in a suitable solvent and used to coat a braided absorbable suture as hereinbefore described.

Data on the various coated sutures prepared and results of the suture evaluation are given in Table II.

EXAMPLES 3-14

Following the procedures of Examples 1 and 2, other poly(alkylene oxalate) copolymers and terpolymers were prepared by reacting diethyl oxalate with mixtures of selected $C_4$ to $C_{10}$ alkanediols. Information on each polymer composition, inherent viscosity, melting point and crystallinity are given in Table I. Braided absorbable surgical suture coated with various amounts of the polymers were prepared and evaluated as shown in Table II.

EXAMPLE 15

32/26/24/18
Poly(tetramethylene-co-hexamethylene-co-octamethylene-co-dodecamethylene oxalate)

Following the procedure of Examples 1 and 2, distilled diethyl oxalate (14.6 g, 0.100 mole), 1,4-butanediol (2.9 g, 0.032 mole), 1,6-hexanediol (3.2 g, 0.027 mole), 1,8-octanediol (3.6 g, 0.024 mole), 1,12-dodecanediol (3.8 g, 0.019 mole), and stannous oxalate (4.1 mg, 0.020 mmole) were added under dry and oxygen-free conditions to a glass reactor equipped with a magnetic stirrer. The mixture was heated under nitrogen at 120° and 160° C for 2 and 1 hours, respectively, while allowing the formed alcohol to distill. The prepolymer was cooled to room temperature, then reheated in vacuo (0.1 mm Hg) to 160° C and maintained at these conditions for 3 hours while continuing to remove distillates. The polymerization was completed by heating at 190° C for 2 hours to obtain a polymer having the properties shown in Table I. Suture tie-down smoothness is improved by coating a braided suture with poly(alkylene oxalate) polymer.

TABLE I

Characterization of Poly(alkylene oxalate) Polymers

| Ex. | Identification | Ratio of alkylene moieties In reaction | Ratio of alkylene moieties In product[a] | $\eta$inh[b] | $T_m$[c] ° C | Crystallinity % |
|---|---|---|---|---|---|---|
| 1 | $C_6$ | 100% | 100% | 0.30 | 70 | — |
| 2 | $C_4/C_{10}$ | 21/79 | (d) | 0.46 | 69 | — |
| 3 | $C_4/C_{10}$ | 50/50 | (d) | 0.08 | 56 | 41 |
| 4 | $C_4/C_{10}$ | 50/50 | (d) | 0.41 | 62 | 41 |
| 5 | $C_4/C_{10}$ | 86/14 | (d) | 0.22 | 84 | 40 |
| 6 | $C_4/C_{10}$ | 33/67 | 23/77 | 0.10 | 65 | 44 |
| 7 | $C_4/C_{10}$ | 7/30 | 72/28 | 0.13 | 56 | 46 |
| 8 | $C_4C_8$ | 33/67 | 22/78 | 0.21 | 68 | 49 |
| 9 | $C_6/C_8$ | 75/25 | 77/23 | 0.17 | 59 | 47 |
| 10 | $C_4/C_6$ | 25/75 | 17/83 | 0.17 | 64 | 46 |
| 11 | $C_4/C_6/C_8$ | 10/80/10 | 3/86/11 | 0.16 | 64 | 44 |
| 12 | $C_4/C_8$ | 33/67 | 24/76 | 0.22 | 68 | 40 |
| 13 | $C_6C_8$ | 73/27 | 73/27 | 0.15 | 54 | 36 |
| 14 | $C_4/C_6/C_8$ | 39/32/29 | 39/39/22 | 0.29 | 50 | 20 |
| 15 | $C_4/C_6/C_8/C_{12}$ | 32/26/24/18 | (d) | 0.46 | 54 | 28 |

TABLE II

Coated Suture Performance

| Ex. | | Coating Solution[a] Solvent composition | Polymer concentration | Coating % add-on | Tie down[c] Dry | Wet | Roughness[d] (lbs) | Appearance and handling |
|---|---|---|---|---|---|---|---|---|
| 1 | (a) | C | 20 | 13[b] | 7.5 | 4 | — | Wiry, surface spots |
|   | (b) | M | 13 | 11[b] | 6.5 | 4 | — | Wiry surface spots |
|   | (c) | M | 13 | 6[b] | 6 | 5 | — | Wiry surface spots |
|   | (d) | M | 13 | 11 | 8 | 4 | — | Good |
| 2 | (a) | C | 20 | 10.5[b] | 4 | 3 | — | Wiry surface spots |
|   | (b) | M | 13 | 6[b] | 4 | 4 | — | Slightly stiff |
|   | (c) | M | 13 | 8[b] | 4 | 4 | — | Slightly stiff |
|   | (d) | M | 11 | 7[b] | 5 | 4 | — | Good |
|   | (e) | M | 13 | 6 | 4 | 4 | — | Good |
| 3 | (a) | M | 35 | 1 | 8 | 7 | 0.5 | Slightly stiff surface spots |
|   | (b) | M | 29 | 3 | — | — | 0.5 | — |
|   | (c) | M | 19 | <1 | 6.5 | 7 | 0.6 | Slightly stiff |
|   | (d) | T | 30 | <1 | — | — | 0.6 | — |
| 4 | (a) | M | 18 | 2 | 6 | 5 | 0.6 | Stiff |
|   | (b) | M | 14 | <1 | — | — | 0.5 | — |
|   | (c) | M | 14 | <1 | — | — | 0.8 | — |
|   | (d) | T | 20 | 4 | 6 | 3.5 | 1.0 | Stiff, some skinning |
|   | (e) | T | 10 | 3 | — | — | 1.2 | — |
| 5 | (a) | M | 30 | 8 | 7 | 6 | 1.5 | Slightly stiff |
|   | (b) | M | 21 | 1 | — | — | 1.8 | — |
|   | (c) | M | 13 | 4 | 5 | 2 | 2.0 | Good |
| 6 |   | M | 7 | 2 | — | — | 3.0 | Good |
| 7 | (a) | M | 3.5 | 1 | — | — | 2.8 | Good |
|   | (b) | M | 7.0 | 2.3 | — | — | 2.8 | Good |
| 8 | (a) | M | 7.0 | 7.0 | — | — | 2.6 | Good |
|   | (b) | M | 10 | 3.9 | — | — | 0.2 | Good |
|   | (c) | M | 15 | 6.0 | — | — | 0.3 | Good |
| 9 | (a) | M | 3.5 | <1 | — | — | 2.5 | Good |
|   | (b) | M | 7.0 | 2.7 | — | — | 2.2 | Good |
| 10 |   | M | 7.0 | 2.7 | — | — | 2.5 | Good |
| 11 |   | M | 7.0 | 2.2 | — | — | 0.2 | Good |

EXAMPLE 16

Biological Testing

Acute systemic toxicity of poly(alkylene oxalate) was determined utilizing poly(hexamethylene oxalate) prepared in accordance with the procedure of Example 1 ($\eta$inh in $CHCl_3$ = 0.64). A 10 percent suspension of the polymer was prepared in a 2 percent pectin solution. Male Swiss-Webster mice were injected interperitoneally with 5000 mg of solution per kg of body weight. Control aninals received 50 ml of pectin per kg body weight. The animals were examined daily for 28 days. The $LD_{50}$ of the poly(alkylene oxalate) was greater than 5000 mg/kg.

Tissue response of sutures coated in accordance with the present invention was determined utilizing a 90/10 poly(glycolide-co-L(-) lactide) suture coated with the poly(alkylene oxalates) of Examples 1, 3, 4 and 5. Samples of coated sutures and uncoated controls were implanted in the gluteal muscles of female Long-Evans rats. Sutures coated with the polymers of Examples 4 and 5 elicited minimal tissue reaction similar to that resulting with the uncoated controls. Sutures coated with the polymers of Examples 1 and 3 evidenced a slightly higher initial tissue reaction than the uncoated controls, but after 7 days tissue reaction was minimal and equivalent to the controls.

The rates of absorption and in vivo tensile strength retention of sutures coated in accordance with the present invention were determined utilizing a 90/10 poly(glycolide-co-L(-)lactide) suture coated with the poly(alkylene oxalates) of Examples 3, 4 and 5. Samples of coated sutures and uncoated controls were implanted subcutaneously in female Long-Evans rats for a period of 5 to 30 days. No significant differences in suture absorption rate or tensile strength retention were observed between the coated sutures and the uncoated controls.

While the foregoing specification and examples have been directed to coating absorbable multifilament, braided sutures, it will be readily appreciated that the coating may likewise be used with good results on absorbable monofilament sutures as well as on nonabsorbable monofilament and multifilament sutures.

Nonabsorbable sutures such as cotton, linen, silk, nylon, polyethylene terephthalate and polyolefins are normally coated with nonabsorbable compositions. Polyolefins are usually of monofilament construction while cotton, linen, silk and polyester are usually of braided, twisted or covered multifilament construction. While there is usually no requirement that the coating on such sutures be absorbable, the composition of the instant invention may, nevertheless, be used as a lubricating finish for nonabsorbable sutures if desired.

In the above examples, the coating solution was applied to the final suture structure in order to provide a substantially continuous coating on the outer surface of the braid. It is understood, however, that the coating may be applied, if desired, to the individual filaments before they are formed into strands or to the individual strands before they are formed into the final suture structure. Also, while all the above examples were conducted with size 2-0 braided suture prepared from a 90/10 glycolide/lactide copolymer, this was for the sake of convenience only, and invention is not limited as to suture size or composition but may be practiced, for example, with sutures from size 9-0 to size 2 and larger, and with other suture materials. The foregoing examples are intended to be merely illustrative, and many modifications and variations thereof will be apparent to those skilled in the art.

What is claimed is:

1. A synthetic, multifilament suture having improved tie-down properties, said suture being coated with from about 1 to 15 percent by weight of a composition comprising a poly(alkylene oxalate) wherein the alkylene is $C_6$ or a mixture of $C_4$- to $C_{12}$-alkylene moieties, said poly(alkylene oxalate) having a melting point below about 100° C and an inherent viscosity of from about 0.1 to 1.2 as determined at 25° C on a 0.1 percent solution of polymer in $CHCl_3$ or hexafluoroisopropanol.

2. A suture of claim 1, wherein the multifilament suture is of a braided construction.

3. A suture of claim 1, wherein said poly(alkylene oxalate) is poly(hexamethylene oxalate).

4. A suture of claim 1, wherein the poly(alkylene oxalate) comprises $C_4$-, $C_6$-, and $C_8$-alkylene oxalate moieties.

5. A suture of claim 4, wherein the $C_6$-alkylene oxalate comprises from about 30 to 80 percent of the total poly(alkylene oxalate), and the $C_4$- and $C_8$-alkylene oxalates each comprise from about 10 to 40 percent of the total poly(alkylene oxalate).

6. A suture of claim 1 wherein the poly(alkylene oxalate) comprises $C_4$-, $C_6$-, $C_8$-, and $C_{12}$-alkylene oxalate moieties.

7. A suture of claim 6 wherein the $C_4$-, $C_6$-, $C_8$-, and $C_{12}$-alkylene oxalates each comprise from about 10 to 40 percent of the total poly(alkylene oxalate).

8. A suture of claim 1 wherein the poly(alkylene oxalate) comprises $C_4$- and $C_{10}$-alkylene oxalate moieties.

9. A suture of claim 8 wherein the $C_4$- and $C_{10}$-alkylene oxalates each comprise from about 10 to 90 percent of the total poly(alkylene oxalate).

10. A suture of claim 1 wherein the poly(alkylene oxalate) comprises $C_4$- and $C_8$-alkylene oxalate moieties.

11. A suture of claim 10 wherein the $C_4$- and $C_8$-alkylene oxalates each comprise from about 10 to 90 percent of the total poly(alkylene oxalate).

12. A suture of claim 1 wherein the poly(alkylene oxalate) comprises $C_4$- and $C_6$-alkylene oxalate moieties.

13. A suture of claim 12 wherein the $C_4$- and $C_6$-alkylene oxalates each comprise from about 10 to 90 percent of the total poly(alkylene oxalate).

14. A suture of claim 1 wherein the poly(alkylene oxalate) comprises $C_6$- and $C_{10}$-alkylene oxalate moieties.

15. A suture of claim 14 wherein the $C_6$- and $C_{10}$-alkylene oxalates each comprise from about 10 to 90 percent of the total poly(alkylene oxalate).

16. A suture of claim 1 wherein the poly(alkylene oxalate) comprises $C_6$- and $C_8$- alkylene oxalate moieties.

17. A suture of claim 16 wherein the $C_6$- and $C_8$-alkylene oxalates each comprise from about 10 to 90 percent of the total poly(alkylene oxalate).

18. A suture of claim 1 coated with from about 5 to 10 percent of the said composition.

19. A suture of claim 2 wherein the synthetic absorbable suture is comprised of homopolymers or copolymers of lactide and glycolide.

20. A suture of claim 19 wherein said suture is comprised of a copolymer derived from 10 weight percent lactide and 90 weight percent glycolide.

21. A suture of claim 20 wherein the multifilament suture is a braided suture.

22. A suture of claim 2 wherein the synthetic absorbable suture is comprised of poly(p-dioxanone).

23. A suture of claim 22 wherein the multifilament suture is of a braided construction.

24. A method for improving the tie-down characteristics of a multifilament suture which comprises coating said suture with from about 1 to 15 percent by weight of a composition comprising a poly(alkylene oxalate) wherein the alkylene is $C_6$ or a mixture of $C_4$ to $C_{12}$ alkylene moieties, said poly(alkylene oxalate) having a melting point below about 100° C and an inherent viscosity of from about 0.1 to 1.2 as determined at 25° C on a 0.1 percent solution of polymer in $CHCl_3$ or hexafluoroisopropanol.

25. The method of claim 24 wherein the poly(alkylene oxalate) is poly(hexamethylene oxalate).

26. The method of claim 24 wherein the poly(alkylene oxalate) comprises alkylene oxalate moieties selected from the group consisting of $C_4$- and $C_6$-, $C_4$- and $C_8$-, $C_4$- and $C_{10}$-, $C_6$- and $C_8$-, and $C_6$- and $C_{10}$-alkylene oxalates.

27. The method of claim 26 wherein each alkylene oxalate is present in an amount equal to from about 10 to 90 percent of the total poly(alkylene oxalate).

28. The method of claim 24 wherein the poly(alkylene oxalate) comprises $C_4$-, $C_6$- and $C_8$-alkylene oxalate moieties.

29. The method of claim 28 wherein the $C_6$-alkylene oxalate comprises from about 30 to 80 percent of the total poly(alkylene oxalate) and the $C_4$- and $C_8$-alkylene oxalates each comprise from about 10 to 40 percent of the total poly(alkylene oxalate).

30. The method of claim 24 wherein the poly(alkylene oxalate) comprises $C_4$-, $C_6$-, $C_8$-, and $C_{12}$-alkylene oxalate moieties.

31. The method of claim 30 wherein the $C_4$-, $C_6$-, $C_8$-, and $C_{12}$-alkylene oxalates each comprise from about 10 to 40 percent of the total poly(alkylene oxalate).

32. The method of claim 24 wherein said suture is composed of an absorbable synthetic polymer selected from the group consisting of homopolymers and copolymers of lactide and glycolide.

33. The method of claim 24 wherein said suture is composed of poly(p-dioxanone).

UNITED STATES PATENT AND TRADEMARK OFFICE
CERTIFICATE OF CORRECTION

PATENT NO. : 4,105,034
DATED : AUGUST 8, 1978
INVENTOR(S) : SHALABY W. SHALABY & DENNIS D. JAMIOLKOWSKI

It is certified that error appears in the above-identified patent and that said Letters Patent are hereby corrected as shown below:

Column 2, line 14: "good tie-down" should read -- good knot tie-down --.
Table I, Example 8, Identification Column: "$C_4C_8$" should read -- $C_4/C_8$ --.
Table I, Example 13, Identification Column: "$C_6C_8$" should read -- $C_6/C_8$ --.
Table I, Example 7, In Reaction Column: "7/30" should read -- 70/30 --.
Table I: All footnotes omitted.
Table II: Examples 12 and 13 and all footnotes should be inserted to appear as per attachment.
Table II, Example 5(b), Coating Add-On Column: "1" should read -- 11 --.
Column 7, line 43: "aninals" should read -- animals --.
Column 8, line 54: "coating may" should read -- coating solution may --.

Signed and Sealed this

First Day of July 1980

[SEAL]

Attest:

SIDNEY A. DIAMOND

Attesting Officer

Commissioner of Patents and Trademarks

TABLE II

Coated Suture Performance

| Example | Coating solution(a) | | Coating % add-on | Tie-down(c) | | Roughness(d) (lbs) | Appearance and handling |
|---|---|---|---|---|---|---|---|
| | Solvent composition | Polymer concentration | | Dry | Wet | | |
| 12(a) | M | — | 2.9 | 7 | 2.5 | — | Good |
| (b) | M | — | 4.3 | 7 | 4.5 | — | Good |
| 13(a) | M | — | 2.5 | 7 | 2 | — | Good |
| (b) | M | — | 4.8 | 8 | 4.5 | — | Good |

(a) Solvent: C = chloroform
T = toluene
M = 2:1 chloroform:trichloroethane

Polymer concentration in grams of polymer/100 ml solvent.

(b) Braid annealed after coating.

(c) Semiquantitative determination: 0 = untreated suture
7 = smoothness of silk (d) Instrumental determination: uncoated control = 3.8 lbs